United States Patent [19]

Hu

[11] Patent Number: 5,663,995

[45] Date of Patent: Sep. 2, 1997

[54] SYSTEMS AND METHODS FOR RECONSTRUCTING AN IMAGE IN A CT SYSTEM PERFORMING A CONE BEAM HELICAL SCAN

[75] Inventor: Hui Hu, Waukesha, Wis.

[73] Assignee: General Electric Company, Milwaukee, Wis.

[21] Appl. No.: 659,203

[22] Filed: Jun. 6, 1996

[51] Int. Cl.$^6$ .................................................. A61B 6/03
[52] U.S. Cl. ........................................... 378/15; 378/901
[58] Field of Search ................................. 378/4, 15, 901

[56] References Cited

U.S. PATENT DOCUMENTS

| | | | |
|---|---|---|---|
| 4,580,219 | 4/1986 | Pelc et al. | 364/413.21 |
| 4,821,210 | 4/1989 | Rumbaugh | 395/121 |
| 5,047,931 | 9/1991 | Lin | 364/413.21 |
| 5,233,518 | 8/1993 | King et al. | 364/413.18 |
| 5,253,171 | 10/1993 | Hsiao et al. | 364/413.19 |
| 5,265,142 | 11/1993 | Hsieh | 378/4 |
| 5,270,923 | 12/1993 | King et al. | 364/413.13 |
| 5,404,293 | 4/1995 | Weng et al. | 378/15 |
| 5,504,792 | 4/1996 | Tam | 378/15 |

OTHER PUBLICATIONS

Crawford et al., Computed Tomography Scanning with Simultaneous Patient Translation, Med. Phys. 17(6), Nov./Dec. 1990, pp. 967–982.

*Primary Examiner*—David P. Porta
*Assistant Examiner*—David Vernon Bruce
*Attorney, Agent, or Firm*—John S. Beulick; John H. Pilarski

[57] ABSTRACT

A method for reconstructing an image in a computed tomography system performing a cone beam helical scan is described. In accordance with one embodiment, a point is selected for which image data is to be generated and a ray pair is identified wherein each ray passes through the selected point. Further, each ray in the ray pair is related according to view angle and detector angle associated with each ray. Projection data of each ray is then weighted to generate image data for the selected point.

14 Claims, 4 Drawing Sheets

SYSTEMS AND METHODS FOR RECONSTRUCTING AN IMAGE IN A CT SYSTEM PERFORMING A CONE BEAM HELICAL SCAN

FIELD OF THE INVENTION

This invention relates generally to computed tomography (CT) imaging and more particularly, to reconstructing images from projection data obtained in cone beam helical scans.

BACKGROUND OF THE INVENTION

In at least one known CT system configuration, an x-ray source projects a fan-shaped beam which is collimated to lie within an X-Y plane of a Cartesian coordinate system, generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object.

One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better control of contrast, improved image reconstruction at arbitrary locations, and better three-dimensional images.

Cone beam helical scanning also is known. A cone beam scan is performed using a multi-dimensional detector array instead of a linear detector array as is used in a fan beam scan. In a cone beam helical scan, the x-ray source and the multi-dimensional detector array are rotated with a gantry within the imaging plane as the patient is moved in the z-axis synchronously with the rotation of the gantry. Such a system generates a multi-dimensional helix of projection data. As compared to fan beam helical scanning, cone beam helical scanning provides improved slice profiles, greater partial volume artifact reduction, and faster patient exam speed.

Generally, in cone beam helical scanning, approximately one-helical-pitch worth of data on each side of the image slice is used to generate the image data. Specifically, image data on each side of the image slice, and 360° apart is interpolated to reconstruct an image slice. The method for generating the image using one-helical-pitch worth of data on each side of the slice is sometimes referred to as a "360° interpolation" method, and is effective in reducing inconsistency artifacts.

The one-helical-pitch interpolation method described above generally requires a total of two-helical-pitch (720°) worth of data to reconstruct each slice, i.e., one-helical-pitch worth of data on each side of the slice. The 360° interpolation method, therefore, does not provide satisfactory results at end regions along the z-axis. Specifically, any slice to be reconstructed within the "first" or "last" helical pitch worth of data along the z-axis does not have the requisite two-helical-pitch worth of data. These end regions are sometimes referred to herein as "dead regions." Moreover, using a long range interpolation to reconstruct slices broadens the slice profile.

Also, in some applications, reduced scanning time or increased volume coverage is required. Without changing other system parameters, the time reduction and coverage increase can be achieved by moving the table faster, which results in each slice being supported by less than 2πr worth of cone beam data.

It would be desirable to provide, in a cone beam helical image reconstruction, a manner for reducing the extent of the dead regions and slice profile broadening. It also would be desirable to enable the table speed to be increased in a cone beam system.

SUMMARY OF THE INVENTION

These and other objects may be attained in a cone beam helical scanning image reconstruction system which, in one embodiment, reduces the extent of the dead regions and slice profile broadening. Specifically, for a slice to be reconstructed, the system identifies ray pairs relating to the slice and uses projection data of the ray pairs to reconstruct the slice. Particularly, by dividing one rotation worth of cone beam data into two groups, and by combining the corresponding rays from each group to compensate for errors caused by the table movement, rays can be identified and utilized to reconstruct an image. A two-dimensional helical extrapolative algorithm may be extended, for example, to three dimensions and used for reconstructing the slice.

Reconstructing an image slice using the above described method requires 180° worth of data on each side of the slice. The method is sometimes referred to herein as a "180° interpolation" method. While still maintaining the effectiveness in reducing inconsistency artifacts, the method also reduces the extent of the dead region on both ends to one half-helical-pitch and facilitates reducing slice profile broadening.

In another aspect, the present invention enable increasing table speed, i.e., a faster scan. More particularly, and with respect to the slice to be reconstructed, the cone beam projection data that have contributions to reconstruction of the slice are identified. The redundant data is weighted so that redundant ray weights have a sum of unity, or one. By limiting the contribution of redundant rays using the above described algorithm, the amount of data required for cone beam helical image reconstruction can be reduced. Reconstructing an image slice using the above described method requires less than 360° worth of data and enables table speed to increase while maintaining image quality.

DETAILED DESCRIPTION OF THE DRAWINGS

Figure 1:
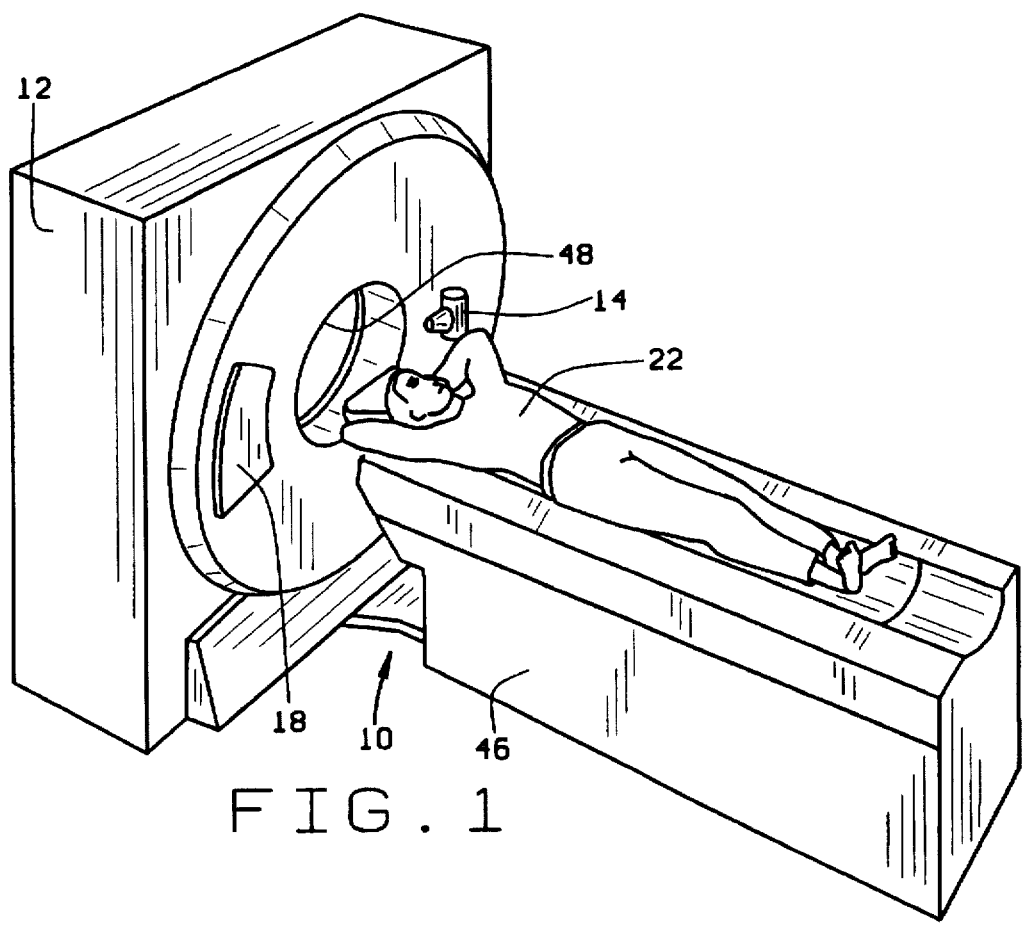
FIG. 1 is a pictorial view of a CT imaging system.
Figure 2:
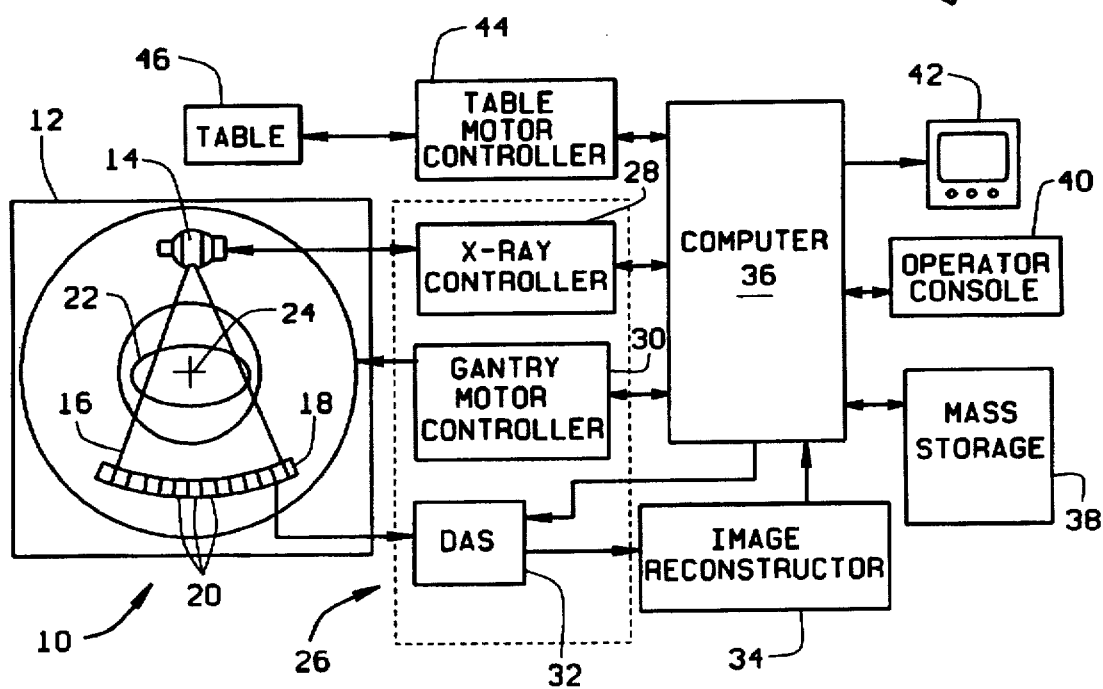
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14, or focal spot, that projects a beam of x-rays 16 toward a detector array 18 on the opposite side of gantry 12. Detector array 18 is formed by detector elements 10 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38. Preferably, the reconstructed image is stored as a data array. The methods described herein may be performed by image reconstructor 34, computer 36, an external computer (not shown), or a combination of such apparatus.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor Controller 44 which controls a motorized table 46 to position patient 22 in gantry 12. Particularly, table 46 moves potions of patient 22 through gantry opening 48.

Figure 3:
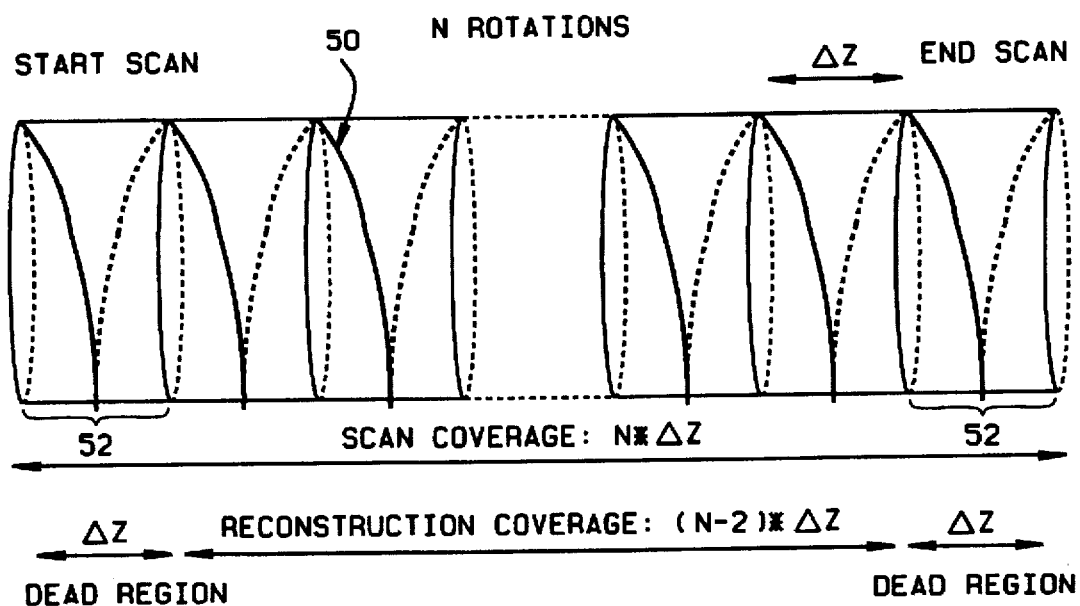
FIG. 3 is a graphic representation of a cone beam helical scan for N gantry revolutions.
Figure 7:
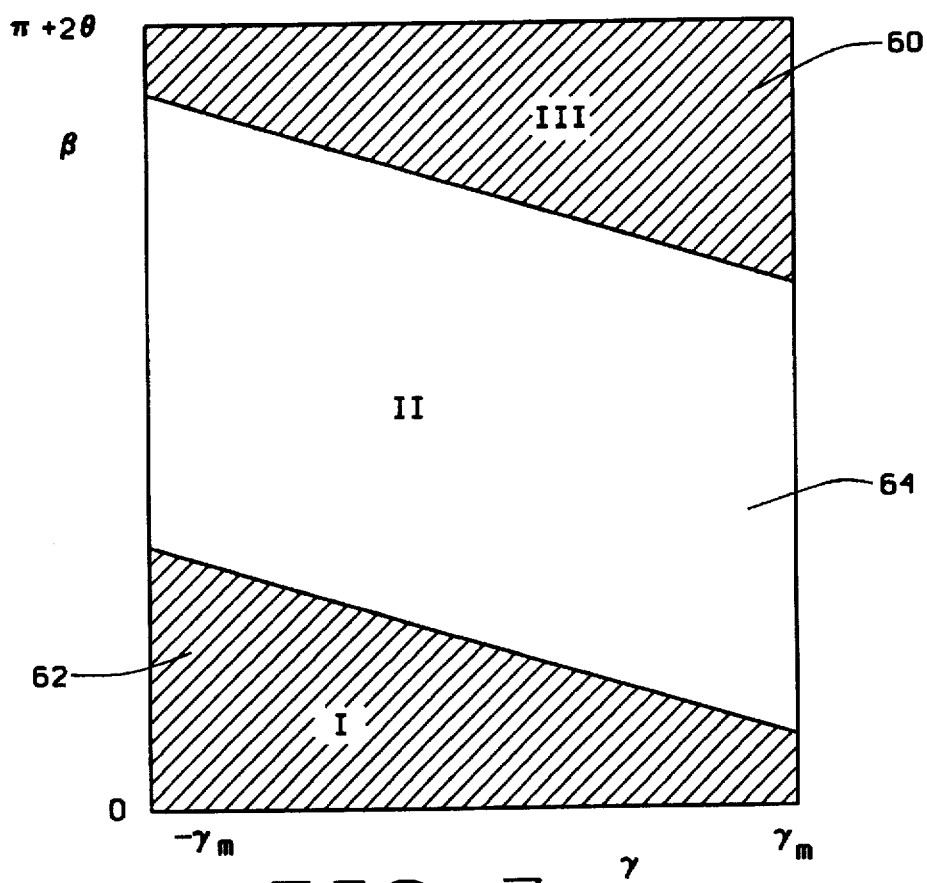
FIG. 7 is a graphic representation of fan beam projection data as a function of gantry angle and detector angle.

Referring to FIG. 3, cone beam three dimensional rays are used to reconstruct an image with two-helical-pitches (720°) worth of data. In helical scanning, gantry 12 translates one helical pitch, $\Delta Z$, in each gantry rotation. The trajectory of x-ray source 14 is shown as line 50. During a scan, gantry 12 translates several (N) helical pitches. As shown in FIG. 7, there are dead regions 52 for which it is difficult to provide a satisfactory image reconstruction. As shown, each dead region 52 is typically one helical pitch, $\Delta Z$, in length.

In one aspect, the present invention is directed to a method for reducing the extent of such dead regions. Specifically, to reduce the extent of such dead regions, and in accordance with one embodiment of the present invention, ray pairs $(\beta_1, \gamma_1, z_1)$ and $(\beta_2, \gamma_2, z_2)$ are identified with respect to a point I to be reconstructed. The projection data corresponding to the ray pair is then weighted to reconstruct the image at point I.

Figure 4A:
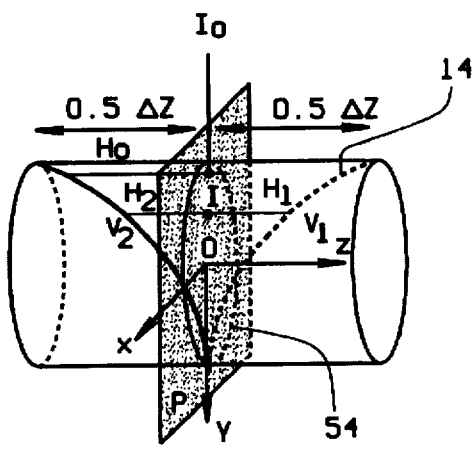
FIG. 4(a) is a graphic representation of a cone beam helical scan during one gantry revolution.
Figure 4B:
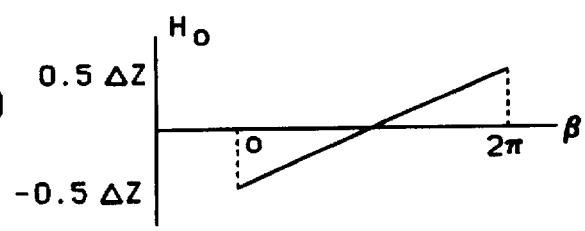
FIG. 4(b) is a geometric representation of the relationship between an x-ray source and view angle β in a cone beam helical scan.
Figure 4C:
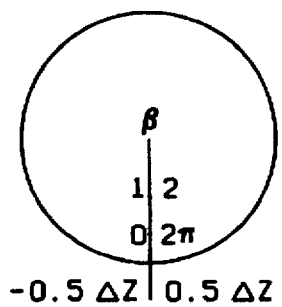
FIG. 4(c) is a geometric representation of gantry rotation in a cone beam helical scan.

To further understand the problem overcome by the present method, FIGS. 4(a), 4(b) and 4(c) indicate data inconsistency in cone beam helical scanning. Specifically, and referring to FIG. 4(a), plane P represents the image to be reconstructed from a helical scan. As shown, plane P is centered in one helical pitch $\Delta Z$ (360°) worth of data. If a distance from x-ray source 14 to plane P is designated as $H_0$, the relationship between $H_0$ and view angle β (or projection angle), as shown in FIG. 4(b), is:

$$\beta = (H_0 \Delta Z + 0.5)\pi. \tag{1}$$

While the source to plane distance, $H_0$, would ideally be zero for every view angle, β, distance $H_0$ is generally non-zero in cone beam scanning. Furthermore, due to the table advancement in helical scanning, the value of H discontinues (from $-0.5\Delta Z$ to $0.5\Delta Z$) in the direction where the first view (β=0) meets the last view (β=2 π) as shown in FIG. 4(c). This discontinuity is known to cause inconsistency artifacts in reconstruction. The larger the value of H, the greater the inconsistency artifacts.

In known cone beam systems, and to reduce inconsistency artifacts, two rays, $(\beta_1, \gamma_1, z_1)$ and $(\beta_2, \gamma_2, z_2)$, from opposite sides of the plane P passing through a point I are used to reconstruct point I in a plane P. The projection data of corresponding rays are $P(\beta_1, \gamma_1, z_1)$ and $P(\beta_2, \gamma_2, z_2)$.

Figure 5:
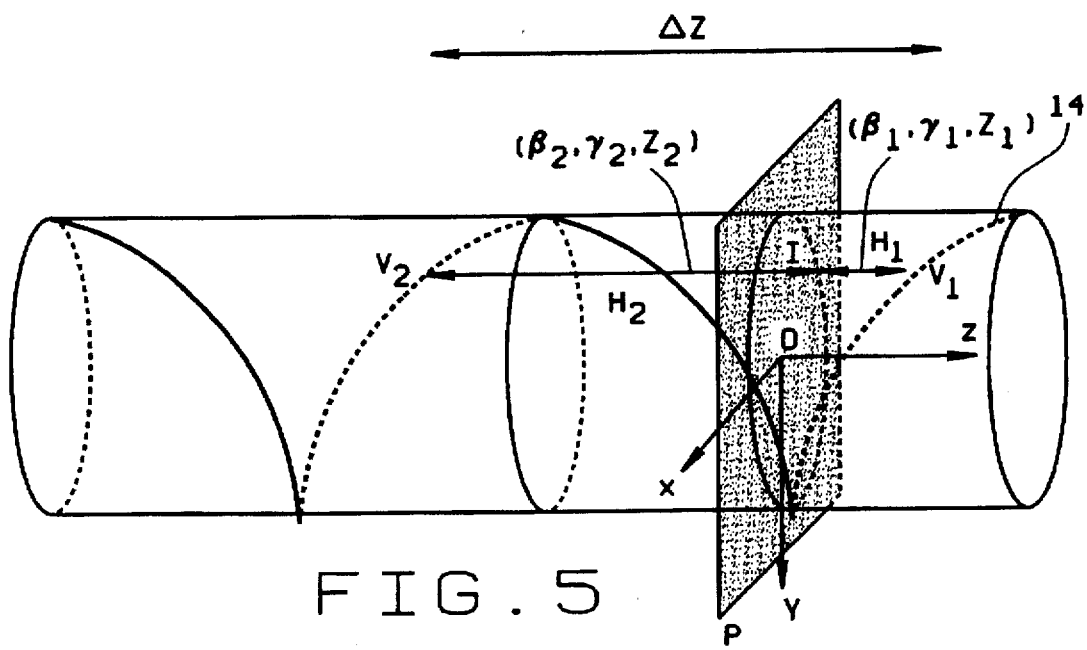
FIG. 5 is a graphic representation of a cone beam helical scan for two gantry revolutions.

For example, and referring specifically to FIG. 5, to reconstruct a point I on the plane P, the data from a view $V_1$ is combined with the corresponding data from a view $V_2$ which is on the other side of the plane P, and one helical pitch, $\Delta Z$ (360°), away from view $V_1$. Using $(\beta_1, \gamma_1, z_1)$ and $(\beta_2, \gamma_2, z_2)$ to denote two rays coming from $V_1$ and $V_2$, respectively, and passing through the point I, the contribution of these two rays to the point I, denoted as $\Delta R$, is:

$$\Delta R = w_1 P(\beta_1, \gamma_1, z_1) + w_2 P(\beta_2, \gamma_2, z_2), \tag{2}$$

where:

$$\beta_2 = \beta_1 - 2\pi, \text{ and} \tag{3a}$$

$$\gamma_2 = \gamma_1, \tag{3b}$$

where 2 π represents that $V_1$ and $V_2$ are 360° apart, i.e., one helical pitch apart, and $w_1$ and $w_2$ are weighting functions.

However, as shown in FIG. 5, reconstructing a slice using this method requires one-helical-pitch (360°) worth of data on each side of the slice. This method does not provide satisfactory reconstructions in regions of one helical pitch length on both ends of the z extent covered by a helical scanning, i.e., dead regions. Moreover, this long range interpolation broadens the slice profiles.

In fan beam helical scanning, it is known to use a helical extrapolation weighting function, $w_{hs}$, to permit reconstruction with 360°, or one rotation, worth of data. However, cone beam projection data space, because of its three-dimensional characteristics, is more complicated than fan beam projection space. Therefore, a helical extrapolation weighting function, $w_{hs}$, is not immediately applicable to cone beam projection data.

In accordance with one embodiment of the present invention, a cone beam helical extrapolation weighting function, $w_{cs}$, is applied to the cone beam projection data. The cone beam helical extrapolation weighting function, $w_{cs}$, in one embodiment, is related to $w_{hs}$, in accordance with the following equation:

$$w_{cs}(\beta,\gamma,z) = w_{hs}(\beta-\beta_0+\pi, \gamma). \quad (4)$$

where $\beta_0$ denotes the view (rotational) angle at which the x-ray beam coincides with the slice to be constructed.

More particularly, weighting function, $w_{cs}$, is applied to three dimensional cone bean projection data to enable reconstruction of a slice from only one rotation worth of data. Therefore, the dead regions are reduced to a half-helical-pitch in length and slice profile broadening is reduced.

In this embodiment of the present invention, images are reconstructed by interpolating data approximately 180° apart. Specifically, one rotation worth of projection data is divided into two groups. Two corresponding rays from the two groups are then combined to compensate for errors caused by the table translation. Particularly, the two corresponding rays passing through the point I on the plane P $(\beta_1,\gamma_1,z_1)$ and $(\beta_2,\gamma_2,z_2)$ satisfy the following relations:

$$\beta_2=\beta_1+\pi-2\gamma_1, \text{ and} \quad (5a)$$

$$\gamma_2=\gamma_1. \quad (5b)$$

The focal spot positions of these two rays need not be on both, i.e., opposing, sides of the plane P.

Both projection data measurements from tiffs ray pair, $P(\beta_1,\gamma_1,z_1)$ and $P(\beta_2,\gamma_2,z_2)$, contribute to the reconstruction of the point I. Particularly, if the ray pair contribution to the point I on the plane P is denoted as $\Delta R$, then:

$$\Delta R = w_{cs1} P(\beta_1,\gamma_1,z_1) + w_{cs2} P(\beta_2,\gamma_2,z_2) \quad (6)$$

where $w_{cs1}$ and $w_{cs2}$ are weighting functions.

As is known, the further the distance, H, i.e., the distance from the focal spot to the plane to be reconstructed, the greater the inconsistency artifacts. Therefore, each ray is weighted according to such distance so that the measurements nearer the plane P will have a larger contribution. For example, let $H_1$ and $H_2$ be the distances from x-ray source 14 to the plane P for these two rays. The weights are given by:

$$w_{cs1} = H_2/(H_2-H_1), \text{ and} \quad (7)$$

$$w_{cs2} = H_1/(H_2-H_1).$$

Given Equation (7), the weights can be written as:

$$w_{cs1} = (\beta_2-\beta_0)/(\beta_2-\beta_1), \text{ and} \quad (8)$$

$$w_{cs2} = (\beta_0-\beta_1)/(\beta_2-\beta_1).$$

For $\beta_0 = \pi$.

Given Equations (5a) and (5b), the weights then become:

$$w_{cs}(\beta,\gamma)=1+(\beta-\pi)/(\pi-2\gamma) \text{ for } 0<\beta<\pi-2\gamma, \text{ and} \quad (9)$$

$$w_{cs}(\beta,\gamma)=1-(\beta-\pi)/(\pi-2\gamma) \text{ for } \pi-2\gamma<=\beta<2\pi.$$

A feathering method can be used to smooth the discontinuity across the line $\beta=\pi-2\gamma$ in the weighting function. This 180° interpolation method thus permits reconstruction of an image with fewer than two gantry rotations in a cone beam scan. When the helical pitch, $\Delta Z$, equals zero, cone beam helical reconstruction reduces to fan beam reconstruction and the cylinder in FIG. 4(a) collapses into circle 54 in the middle. In this extreme case, the ray pair represents two redundant data measured from opposite directions. The 180° interpolation method, as described above, thus permits reconstruction of an image by interpolating data only approximately 180° apart. As a result, the dead regions and slice profile broadening are reduced.

Figure 6:
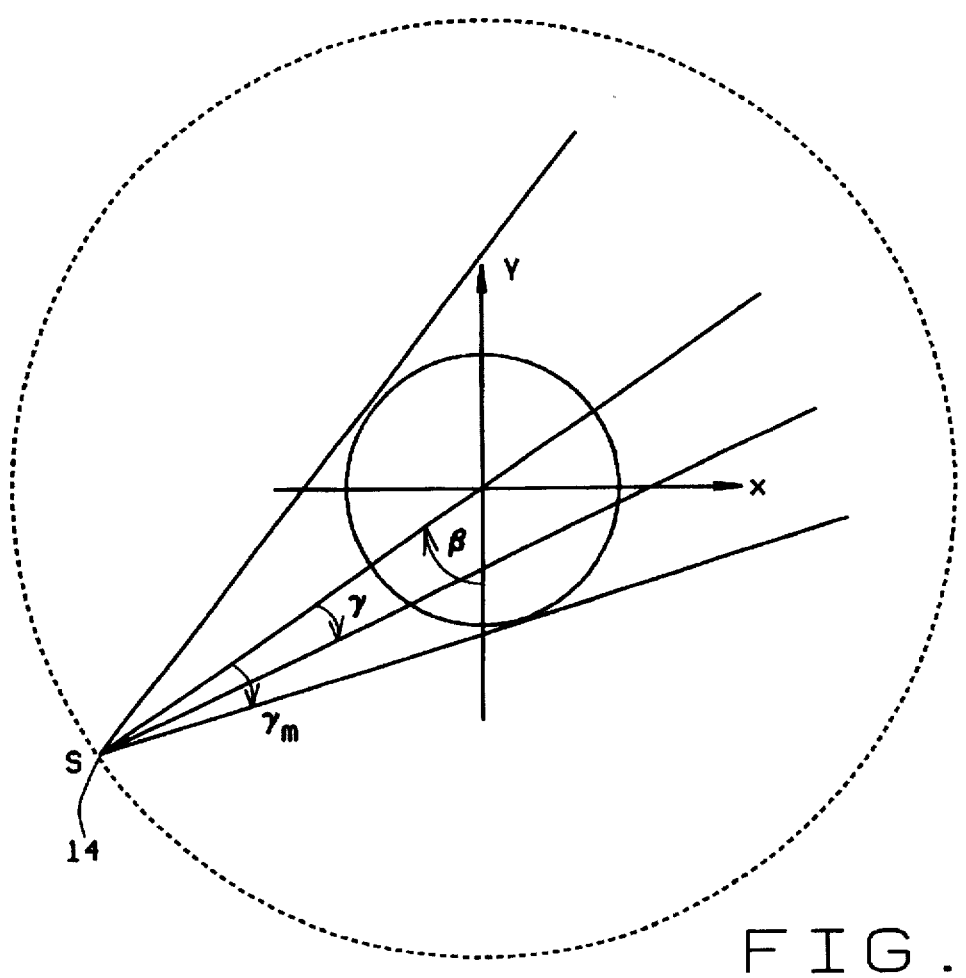
FIG. 6 is a geometric representation of a fan beam.

In another aspect, the present invention enables increasing the table speed. More specifically, and in one embodiment, cone beam three dimensional rays are used to reconstruct an image slice with less than 360° worth of data. For example, and referring to FIG. 6, during a fan beam half-scan, x-ray source 14 projects x-rays 16 at a projection angle $\beta$ and a fan angle $\gamma_m$. Detector array 18 receives the x-rays at a detector angle $\gamma$ and generates projection data, or attenuation measurements. Let $\beta_0$ denote the projection angle at which x-ray source 14 coincides with the slice to be reconstructed. The projection measurements are sometimes redundant. Specifically, measurements along the same line in opposite directions contain same information, except for noise. The two rays on such line, or ray pair $(\beta_1, \gamma_1)$, $(\beta_2, \gamma_2)$, satisfy the equation:

$$\beta_2=\beta_1+\pi+2\gamma_1, \text{ and} \quad (10a)$$

$$\gamma_2=-\gamma_1.$$

In such circumstances, ray $(\beta_1, \gamma_1)$ is the mirror ray of $(\beta_2, \gamma_2)$.

As shown in FIG. 7, fan beam projection data may be classified as either redundant, i.e., corresponding to a ray pair, or non-redundant. In FIG. 7, the redundant data is indicated by shaded regions 60 and 62. Specifically, FIG. 7 depicts fan-beam projection data relating to projection angle $\beta$, where $0<\beta<\pi+2\Theta$, $\Theta \geq \gamma_m$. A ray in unshaded region 64 does not have a mirror ray in the fan-beam half-scan data set. To avoid gross shading due to this non-uniform sampling density, it is known to weight redundant rays in the fan-beam half-scan data set so that the sum of their weights equals unity:

$$w_{FBHS}(\beta_1, \gamma_1) + w_{FBHS}(\beta_1+\pi+2\gamma_1, -\gamma_2) = 1, \quad (11)$$

where $w_{FBHS}(\beta,\gamma)$ is a weighting function applied to the fan-beam half-scan projection data. The weighting functions are generally smoothed to avoid producing artifacts. For example, in accordance with one known weighting method, the following function can be used:

$$w_{FBHS}(x(\beta,\gamma))=3x^2-2x^3, \quad (12)$$

where:

$$x(\beta,\gamma) = \begin{cases} \beta/(2\theta - 2\gamma) & 0 \leq \beta \leq 2\theta - 2\gamma, \\ 1 & 2\theta - 2\gamma < \beta < \pi - 2\gamma, \text{ and} \\ (\pi + 2\theta - \beta)/(2\theta + 2\gamma) & \pi - 2\gamma \leq \beta < \pi + 2\theta. \end{cases} \quad (13)$$

Figure 8:
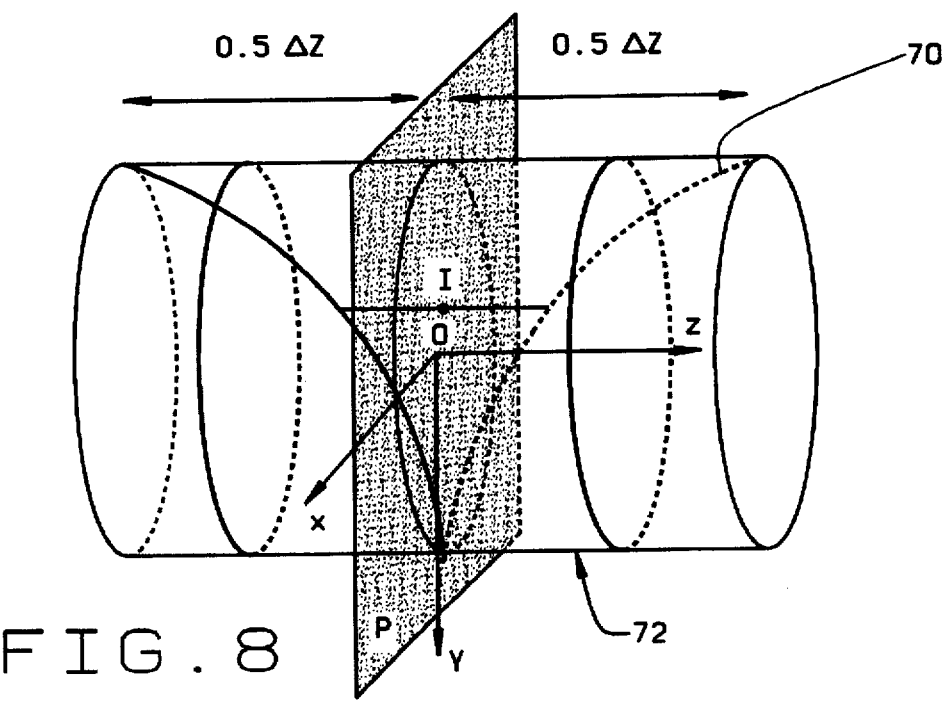
FIG. 8 is a graphic representation of a cone beam scan for one revolution of the gantry.

Projection data for cone beam helical scans, however, is more complicated because of the multi-dimensional characteristics of detector array 18. Referring to FIG. 8, gantry 12 translates one helical pitch ($\Delta Z$) in each gantry rotation, with the trajectory of x-ray source 14 indicated by line 70. With cone beam helical scans, projection data is acquired, and a resulting image is constructed, using three dimensional rays ($\beta$, $\gamma$, Z). Therefore, the fan beam half-scan algorithm described above is not immediately applicable to cone beam helical scan projection data.

One aspect of the present invention is to enable table speed to be increased without sacrificing image quality in a cone beam helical scan. If table 46 moves along the z-axis and through gantry opening 48 so that plane P is only supported by $\Theta$ worth of data, where $2\pi > \Theta > \pi +$ fan angle, the focal spot trajectory of this portion of the cone-beam data is within the region outlined by a highlighted cylinder 72.

In accordance with one embodiment of the present invention, a cone beam half-scan weighting function, $W_{CBHS}$, is applied to the cone beam projection data ($\beta,\gamma,z$). This cone beam half-scan weighting function is related to $W_{FBHS}$ according to the equation:

$$W_{CBHS}(\beta,\gamma,z) = W_{FBHS}(\beta - \beta_0 + \Theta/2, \gamma). \quad (14)$$

By multiplying the weighting to the cone beam projection data as suggested above, an image may be reconstructed with less than one gantry rotation worth of data. Therefore, the table speed can be increased without sacrificing image quality. Although the above description assumes cone beam helical scanning, the method can also be applied to the cone beam step and shoot scanning.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, although the embodiments of the invention are described herein in the context of a cone beam helical scanning system, the present invention could be used in a cone beam step and shoot scanning system. Accordingly, the spirit and scope of the invention are to be limited only by the terms of the appended claims.

What is claimed is:

1. A method for reconstructing an image at a point I using data collected in one rotation of a gantry of a computed tomography system performing a cone beam helical scan, said method comprising the steps of:

identifying a ray pair denoted as ($\beta_1$, $\gamma_1$, $z_1$) and ($\beta_2$, $\gamma_2$, $z_2$) where $\beta$ is a view angle, $\gamma$ is a detector angle, and z is a z-axis location, each ray of the ray pair passing through the point I and:

$\beta_2 = \beta_1 + \pi - 2\gamma$, and $\gamma_2 = -\gamma_1$, and using projection data of each ray, denoted as P($\beta_1$, $\gamma_1$, $z_1$) and P($\beta_2$, $\gamma_2$, $z_2$,) to generate the image data for point I.

2. A method in accordance with claim 1 further comprising the step of weighting the projection data P($\beta_1$, $\gamma_1$, $z_1$) and P($\beta_2$, $\gamma_2$, $z_2$).

3. A method in accordance with claim 2 wherein the contribution of each ray of the ray pair to generating the image data for point I is denoted as $\Delta R$, and:

$$\Delta R = w_{cs1} P(\beta_1, \gamma_1, z_1) + w_{cs2} P(\beta_2, \gamma_2, z_2),$$

where $w_{cs1}$ and $w_{cs2}$ are weighting factors.

4. A method in accordance with claim 2 wherein weighting function $w_{cs}$ is related to a helical scan weighting function $w_{hs}$ and an initial view angle $\beta_0$ so that:

$$w_{cs}(\beta,\gamma,z) = w_{hs}(\beta - \beta_0 + \pi, \gamma).$$

5. A method in accordance with claim 4 wherein weighting the projection data P($\beta_1$, $\gamma_1$, $z_1$) and P($\beta_2$, $\gamma_2$, $z_2$) is performed in accordance with a weighting function defined as:

$$w_{cs}(\beta,\gamma) = 1 + (\beta - \pi)/(\pi - 2\gamma) \text{ for } 0 \leq \beta < \pi - 2\gamma, \text{ and}$$

$$w_{cs}(\beta,\gamma) = 1 - (\beta - \pi)/(\pi + 2\gamma) \text{ for } \pi - 2\gamma \leq \beta < 2\pi.$$

6. A method in accordance with claim 5 wherein a feathering method is used to smooth a discontinuity at $\beta = \pi - 2\gamma$.

7. A system for reconstructing an image at a point I from data collected in one rotation of a gantry of a computed tomography system performing a cone beam helical scan, said system configured to:

identify a ray pair denoted as ($\beta_1$, $\gamma_1$, $z_1$) and ($\beta_2$, $\gamma_2$, $z_2$) where $\beta$ is a view angle, $\gamma$ is a detector angle, and Z is a z-axis location, each ray of the ray pair passing through the point I and:

$\beta_2 = \beta_1 + \pi - 2\gamma$, and $\gamma_2 = -\gamma_1$, and use projection data of each ray denoted as P($\beta_1$, $\gamma_1$, $z_1$) and P($\beta_2$, $\gamma_2$, $z_2$) to generate the image data for point I.

8. A system in accordance with claim 7 further configured to weight the projection data P($\beta_1$, $\gamma_1$, $z_1$) and P($\beta_2$, $\gamma_2$, $z_2$).

9. A system in accordance with claim 7 wherein the contribution of each ray of the ray pair to generate the image data for point I is denoted as $\Delta R$, and:

$$\Delta R = w_{cs1} P(\beta_1, \gamma_1, z_1) + w_{cs2} P(\beta_2, \gamma_2, z_2),$$

where $w_{cs1}$ and $w_{cs2}$ are weighting factors.

10. A system in accordance with claim 8 wherein weighting function $w_{cs}$ is related to a helical scan weighting function $w_{hs}$ and an initial view angle $\beta_0$ so that:

$$w_{cs}(\beta,\gamma,z) = w_{hs}(\beta - \beta_0 + \pi, \gamma).$$

11. A system in accordance with claim 10 wherein the projection data P($\beta_1$, $\gamma_1$, $Z_1$) and P($\beta_2$, $\gamma_2$, $Z_2$) is weighted in accordance with a weighting function defined as:

$$w_{cs}(\beta,\gamma) = 1 + (\beta - \pi)/(\pi - 2\gamma) \text{ for } 0 \leq \beta < \pi - 2\gamma, \text{ and}$$

$$w_{cs}(\beta,\gamma) = 1 - (\beta - \pi)/(\pi + 2\gamma) \text{ for } \pi - 2\gamma \leq \beta < 2\pi.$$

12. A system in accordance with claim 11 wherein a feathering method is applied to smooth a discontinuity at $\beta = \pi - 2\gamma$.

13. A method for reconstructing an image at a point I from projection data collected by a computed tomography system performing a cone beam helical scan, said method comprising the steps of:

identifying a ray pair denoted as ($\beta_1,\gamma_1$) and ($\beta_2,\gamma_2$) where $\beta$ is a view angle and $\gamma$ is a detector angle, so that:

$\beta_2 = \beta_1 + \pi + 2\gamma_1$, and $\gamma_2 = -\gamma_1$, weighting redundant rays with a weighting function, and using the weighted projection data rays to generate the image data for point L.

14. A method in accordance with claim 13 wherein the weighting function $w_{CBHS}$ is related to a fan beam helical scan weighting function $w_{FBHS}$ and an initial view angle $\beta_o$ so that:

$$w_{CBHS}(\beta,\gamma,z) = w_{FBHS}(\beta-\beta_o+\Theta/2, \gamma).$$

* * * * *